(12) United States Patent
Matsumura et al.

(10) Patent No.: US 7,876,929 B2
(45) Date of Patent: Jan. 25, 2011

(54) PERSONAL IDENTIFICATION DEVICE

(75) Inventors: Takafumi Matsumura, Hitachinaka (JP); Akio Nagasaka, Kokubunji (JP); Takafumi Miyatake, Hachiouji (JP)

(73) Assignee: Hitachi, Ltd., Tokyo (JP)

( * ) Notice: Subject to any disclaimer, the term of this patent is extended or adjusted under 35 U.S.C. 154(b) by 980 days.

(21) Appl. No.: 11/663,293

(22) PCT Filed: Oct. 4, 2004

(86) PCT No.: PCT/JP2004/014586

§ 371 (c)(1),
(2), (4) Date: Mar. 20, 2007

(87) PCT Pub. No.: WO2006/038276

PCT Pub. Date: Apr. 13, 2006

(65) Prior Publication Data

US 2008/0075330 A1    Mar. 27, 2008

(51) Int. Cl.
*G06K 9/00* (2006.01)
(52) U.S. Cl. ..................................... 382/115; 382/124
(58) Field of Classification Search ................ 382/115, 382/124; 362/317, 326, 331, 551, 559, 23, 362/26, 27, 600, 611, 612, 582, 327; 250/200, 250/216, 234, 235, 236, 559.01, 559.29, 250/559.36; 349/56, 84, 86, 89; 359/1, 15, 359/17; 313/110, 113; 252/299.01; 348/61, 348/65, 68, 70
See application file for complete search history.

(56) References Cited

U.S. PATENT DOCUMENTS

| | | | |
|---|---|---|---|
| 4,681,435 A | 7/1987 | Kubota et al. | |
| 5,446,290 A | * 8/1995 | Fujieda et al. | ............. 250/556 |
| 6,553,134 B1 | 4/2003 | Amano et al. | |
| 6,856,383 B1 | 2/2005 | Vachris et al. | |
| 2003/0090650 A1 | 5/2003 | Fujieda | |

FOREIGN PATENT DOCUMENTS

| | | |
|---|---|---|
| EP | 1 022 675 A2 | 7/2000 |
| JP | 59-153514 U | 10/1984 |
| JP | 6-72291 A | 3/1994 |
| JP | 6-325158 A | 11/1994 |
| JP | 10-127609 A | 5/1998 |

(Continued)

OTHER PUBLICATIONS

International Search Report dated Nov. 30, 2004 including English translation of pertinent portion (Five (5) pages).

(Continued)

*Primary Examiner*—Sheela C Chawan
(74) *Attorney, Agent, or Firm*—Crowell & Moring LLP

(57) ABSTRACT

A thin personal identification device that in which the infrared light source, transmission light quantity control element array, and light receiving element array are positioned on the same side of a living body. A microcomputer controls the array to combine a first image, which is obtained from the living body when one region of the living body is radiated with light transmitted from the infrared light source, with a second image, which is obtained when another region of the living body is radiated, and identifies a person in accordance with the combined image.

8 Claims, 13 Drawing Sheets

FOREIGN PATENT DOCUMENTS

| | | |
|---|---|---|
| JP | 10-208022 A | 8/1998 |
| JP | 2000-207535 A | 7/2000 |
| JP | 2001-52151 A | 2/2001 |
| JP | 2001-184507 A | 7/2001 |
| JP | 2001-515746 A | 9/2001 |
| JP | 2003-30632 A | 1/2003 |
| WO | WO 99/12472 A1 | 3/1999 |

OTHER PUBLICATIONS

European Search Report dated Oct. 10, 2008.
European Search Report dated Mar. 1, 2010 (Six (6) pages).
International Preliminary Examination Report with English translation (Nine (9) pages).

* cited by examiner

PERSONAL IDENTIFICATION DEVICE

TECHNICAL FIELD

The present invention relates to a personal identification device that uses biometric feature information, and more particularly to a personal identification device that uses a finger's blood vessel pattern as biometric feature information.

BACKGROUND ART

Keys have been used to unlock automobile doors or start up an automobile engine. However, when a key is used for such purposes, a malicious person other than an automobile owner might drive an automobile, for instance, by stealing the key or by picking a lock.

Under the above circumstances, a security enhancement method is disclosed, for instance, by JP-A-61-53972 and JP-A-6-72291. This method provides enhanced security by using a fingerprint, which is biometric feature information, as means of personal identification instead of a key for automobile door unlocking and engine startup.

However, fingerprints can be forged. Therefore, another security enhancement method is disclosed, for instance, by JP-A-2001-184507 and JP-A-2003-30632. This method provides enhanced security by using an image containing a finger's blood vessel pattern, which differs from one person to another, as biometric feature information. This method radiates a finger with a light source containing an infrared or near-infrared light component (hereinafter referred to as an infrared light source). The infrared or near-infrared light is then transmitted through the finger and radiated from the finger. The intensity distribution of the resulting infrared or near-infrared radiation contains the information about a blood vessel pattern (mainly a vein pattern) of the finger. This blood vessel pattern is detected by image pickup means and compared with a preregistered blood vessel pattern to judge whether they match. When they match, personal authentication is achieved because it is concluded that the detected blood vessel pattern belongs to a person having the blood vessel pattern which was pre-registered.

Further, a device similar to a personal identification device that provides personal authentication by using a finger's blood vessel pattern as biometric feature information is disclosed, for instance, by JP-A-10-127609. This device uses an infrared light source to radiate a living body with infrared light, picks up the resulting light reflection with image pickup means, and uses an image containing a blood vessel pattern.

Patent Document 1: JP-A-61-53972
Patent Document 2: JP-A-6-72291
Patent Document 3: JP-A-2001-184507
Patent Document 4: JP-A-2003-30632
Patent Document 5: JP-A-10-127609

DISCLOSURE OF INVENTION

Problem to be Solved by the Invention

However, the method disclosed by JP-A-2003-30632 uses a configuration in which a finger is sandwiched between the light source and image pickup means. Thus, the device is large in size. Consequently, the device cannot readily be mounted, for instance, in an automobile in which the available space is limited.

Meanwhile, when the light source and image pickup means are positioned on the same side of a finger, the thickness (size) of the device can be reduced. However, the image pickup means detects not only the light radiated from the finger, which should be detected, but also the resulting light reflection, which is noise. Therefore, the use of this configuration degrades the image quality.

An object of the present invention is to provide a thin personal identification device that produces a high-quality image.

Means for Solving the Problem (1) To achieve the above object, the present invention provides a personal identification device that includes an infrared light source, a transmission light quantity control element array, and a light receiving element array. The transmission light quantity control element array includes a plurality of light transmission control elements for exercising control to transmit or block light that is radiated from the infrared light source to a living body. The light receiving element array includes a plurality of light receiving elements for receiving light that is radiated from the living body. The infrared light source, the transmission light quantity control element array, and the light receiving element array are positioned on the same side of the living body. The present invention further includes control identification means for identifying a person in accordance with a combined image that is obtained by combining a first image with a second image. The first image is obtained when the light receiving element array acquires light containing internal biometric feature information that is derived from the living body when the transmission light quantity control element array is controlled to radiate one region of the living body with light transmitted from the infrared light source. The second image is obtained when the light receiving element array acquires light containing internal biometric feature information that is derived from the living body when the transmission light quantity control element array is controlled to radiate another region of the living body with light transmitted from the infrared light source. When the present invention is configured as described above, it provides a thin personal identification device that produces a high-quality image.

(2) It is preferred that the transmission light quantity control element array, which is included in the personal identification device according to (1) above, be made of a liquid-crystal material.

(3) It is preferred that the transmission light quantity control element array and the light receiving element array, which are included in the personal identification device according to (1) above, be formed on a single transparent substrate.

(4) It is preferred that an optical element be positioned toward a light receiving surface of the light receiving element array, which is included in the personal identification device according to (1) above, to permit the transmission of only a light component that is vertically incident on the light receiving surface.

(5) It is preferred that at least the infrared light source, the transmission light quantity control element array, and the light receiving element array, which are included in the personal identification device according to (1) above, have a curved surface shape.

(6) It is preferred that the infrared light source, which is included in the personal identification device according to (1) above, include a plurality of infrared light sources, and that some of the plurality of infrared light sources illuminate in accordance with a region radiated by the transmission light quantity control element array.

(7) It is preferred that a light shielding plate be positioned between adjacent pairs of the plurality of infrared light sources, which are included in the personal identification device according to (6) above.

(8) It is preferred that the personal identification device according to (1) above further include a light absorber, which is positioned in a direction in which no light is radiated from the infrared light source.

EFFECTS OF THE INVENTION

The present invention provides a thin personal identification device that produces a high-quality image.

DESCRIPTION OF REFERENCE NUMERALS

10: Personal identification device
20: Microcomputer
30, 31, 32: Infrared light source
40, 41, 42: Transmission light quantity control element array
50: Light receiving element array

BEST MODE FOR CARRYING OUT THE INVENTION

The configuration and operation of a personal identification device according to a first embodiment of the present invention will now be described with reference to FIGS. 1 to 7.

First of all, the overall configuration of the personal identification device according to the first embodiment will be described with reference to FIGS. 1 and 2.

Figure 1:
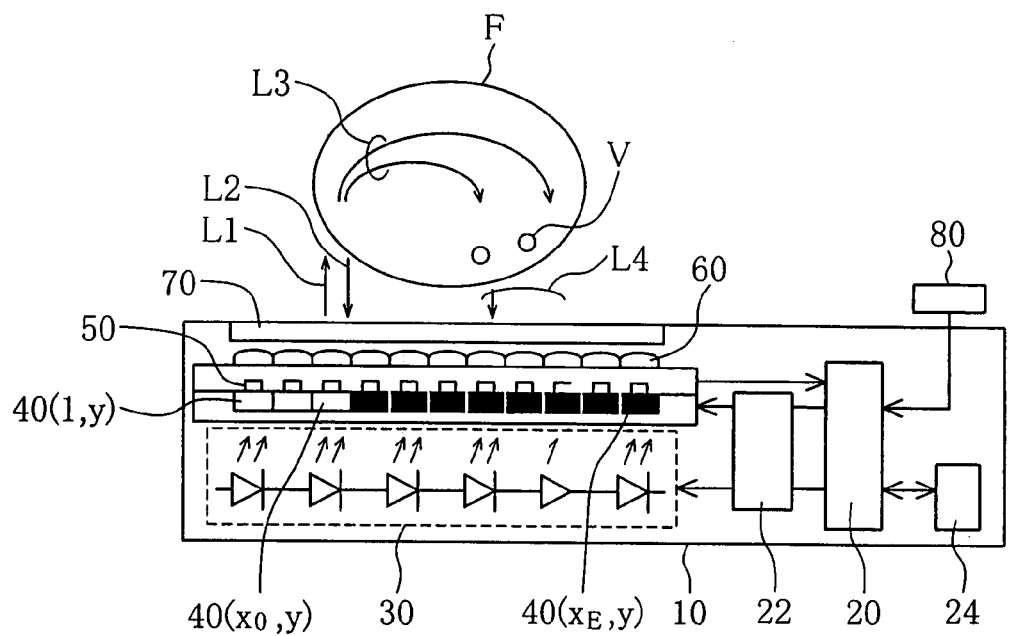
FIG. 1 is a cross-sectional view illustrating the configuration of a personal identification device according to a first embodiment of the present invention.

FIG. 1 is a cross-sectional view illustrating the configuration of the personal identification device according to the first embodiment of the present invention. FIG. 2 is a perspective view illustrating the configuration of the personal identification device according to the first embodiment of the present invention. FIG. 1 is a cross-sectional view taken along a plane perpendicular to the axis of a finger F that is to be identified by the personal identification device 10.

The personal identification device 10 includes a microcomputer 20, a drive circuit 22, a nonvolatile memory 24, an infrared light source 30, a transmission light quantity control element array 40, a light receiving element array 50, a plane lens array 60, a window 70, and a switch 80.

The microcomputer 20 illuminates the infrared light source 30 by applying power to the infrared light source 30 via the drive circuit 22. The microcomputer 20 also irradiates the finger F with infrared light through the transmission light quantity control element array 40. For example, a light emitting diode that emits infrared light or near-infrared light having a wavelength between 800 nm and 950 nm may be used as the infrared light source 30. A plurality of light emitting diodes are arranged in a two-dimensional lattice pattern. The transmission light quantity control element array 40 can block or transmit the light emitted from the infrared light source 30, and increase or decrease the quantity of transmitted light when the emitted light is transmitted. For example, a two-dimensional lattice panel made of liquid crystals that can control the transmission light quantity in accordance with an applied voltage is used as the transmission light quantity control element array 40. In the example shown in the figure, the light is not blocked by the left-hand, approximately ⅓ portion of the transmission light quantity control element array 40, which is shown in white, and the light is blocked by the right-hand, approximately ⅔ portion of the transmission light quantity control element array 40, which is shown in black. The transmission light quantity control element array 40 will be described in detail later with reference to FIG. 3. A method of controlling the transmission light quantity while the light is not blocked by the transmission light quantity control element array 40 will be described later with reference to FIG. 7.

When the light emitted from the infrared light source 30 is not blocked by the left-hand, approximately ⅓ portion of the transmission light quantity control element array 40 as shown in the figure, it is transmitted through the transmission light quantity control element array 40 and shed on the finger F as infrared light L1. Part of the infrared light L1 directly bounces off the surface of the finger F and turns out to be reflected light L2. The remaining transmitted component is scattered within the finger F as scattered light L3 and absorbed by hemoglobin in blood within a blood vessel V. After being scattered and absorbed by the blood vessel V, the infrared light is radiated again from the inner surface (flexor surface) of the finger F as radiant light L4. The radiant light L4, which contains a blood vessel pattern and is radiated again, is transmitted through the window 70. The light scattered at the surface of the finger is condensed by the individual lenses of the plane lens array 60 and shed on each element of the light receiving element array 50. The light receiving element array 50 is a two-dimensional lattice array that uses individual photoelectric conversion elements to convert light to an electrical signal. The lenses of the lens array 60 correlate to the individual elements of the light receiving element array 50 on a one-to-one basis and are arranged in a two-dimensional lattice pattern. An image containing a blood vessel pattern that is imaged by the light receiving element array 50 is converted to an electrical signal due to a photoelectric conversion process, input into the microcomputer 20 when the switch 80 is turned on, and used for personal identification. The microcomputer 20 performs a personal identification process depending on whether a personal blood vessel pattern stored in the memory 24 coincides with the blood vessel pattern detected from the finger F.

When the transmission light quantity control element array 40 and light receiving element array 50 are formed on a single transparent substrate that looks like a sheet of glass, it is possible to reduce the man-hour requirements for personal identification device assembly and decrease the thickness of the personal identification device. The transparent substrate need not be transparent at all wavelengths. The characteristics of the transparent substrate should be such that it is transparent at wavelengths emitted from the infrared light source 30.

The window 70 is used to protect the plane lens array 60. However, it may incorporate a function for transmitting only the light having a wavelength within a waveband of the infrared light source and making the interior invisible from the outside.

Figure 2:
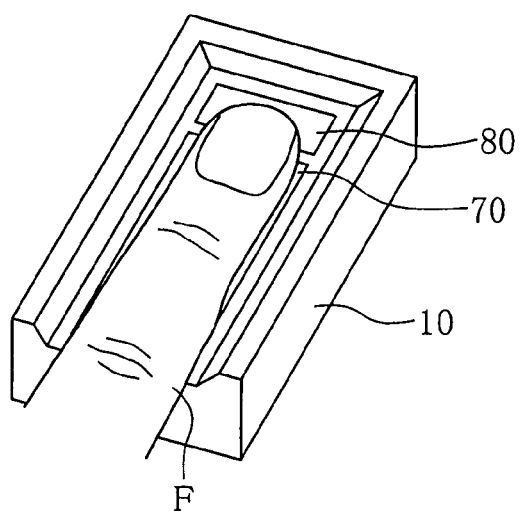
FIG. 2 is a perspective view illustrating the configuration of the personal identification device according to the first embodiment of the present invention.

As shown in FIG. 2, the window 70 and switch 80 are mounted on the upper surface of the personal identification device 10. When a personal identification process is to be performed, the finger F is placed on the window 70 and switch 80 as shown in the figure. A switch having a microswitch contact or the like is used as the switch 80. When pressed by the finger F, the switch 80 turns on. A capacitance switch, photoelectric switch, or other similar switch may also be used as the switch 80. When the upper surface height of the switch 80 is slightly higher (e.g., 2 or 3 mm higher) than the height of the window 70, the central part of the finger F is positioned above the window 70 while the end of the finger F is in contact with the switch 80. If the finger F is pressed against the window 70, a vein positioned inside the finger F but close to the surface may be squashed so that the blood vessel pattern looks different. To avoid erroneous identification due to a squashed blood vessel, it is preferred that the finger F be positioned above the window 70.

The layout of the transmission light quantity control element array 40 and light receiving element array 50 for use in the personal identification device according to the present embodiment will now be described with reference to FIG. 3.

Figure 3:
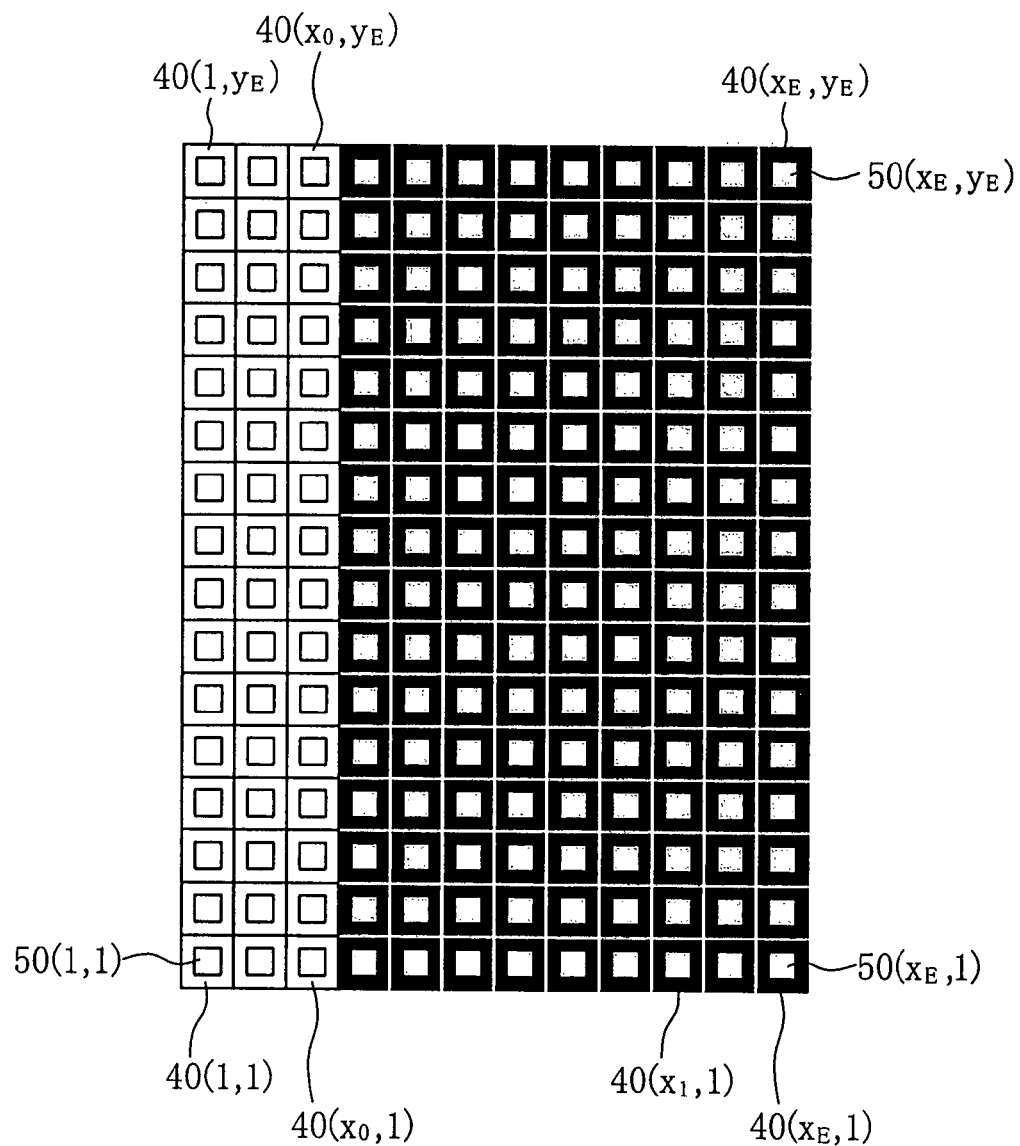
FIG. 3 is a plan view illustrating the layout of a transmission light quantity control element array and a light receiving element array, which are used in the personal identification device according to the first embodiment of the present invention.

FIG. 3 is a plan view illustrating the layout of the transmission light quantity control element array 40 and light receiving element array 50 that are used in the personal identification device according to the first embodiment of the present invention.

As shown in FIG. 3, the transmission light quantity control element array 40 includes elements that are arranged in a lattice pattern. More specifically, the transmission light quantity control element array 40 includes xE horizontal elements and yE vertical elements. It is a two-dimensional lattice array that uses individual elements to arbitrarily control the quantity of light to be transmitted. The transmission light quantity control element array 40 is made, for instance, of a liquid-crystal material that is configured as a lattice array. The voltage applied between electrodes on both ends of a liquid crystal is varied to vary the polarization amount of transmitted light. When the resulting light passes through a polarization plate, the quantity of light to be transmitted can be controlled in accordance with a polarization angle. This method makes it easy to control the quantity of infrared light transmission and is widely used. Therefore, the present embodiment can be implemented at a low cost. For example, 100 horizontal elements and 140 vertical elements may be arranged in a lattice pattern. The region of such elements may be 3 cm wide and 4.2 cm high. The number of infrared light sources need not be equal to the number of elements within the transmission light quantity control element array 40. When the transmission light quantity control element array 40 is a lattice array that includes 100 horizontal elements and 140 vertical elements, the infrared light source 30 may be a lattice array that includes 5 horizontal light-emitting diodes and 4 vertical light-emitting diodes.

The microcomputer 20 operates the drive circuit 22 to control the transmission light quantity control element array 40 in such a manner that, for example, the light is transmitted through a certain portion ((1, 1) to (x0, yE), shown in white in the figure) of the transmission light quantity control element array 40 while the light is blocked by the remaining portion (shown in black in the figure). The light is then shed on a limited area of the finger F. The region of light transmission is not always shaped like a strip as shown in the figure. In other words, the light transmission region may be trapezoidal, a single spot, or in any other shape.

As shown in FIG. 1, the infrared light L1 transmitted through the transmission light quantity control element array 40 partly bounces off the surface of the finger F and turns out to be reflected light L2, and the remaining transmitted component is scattered within the finger F or absorbed by hemoglobin in blood within a blood vessel V. The scattered or absorbed infrared light L3 is radiated again from the inner surface (flexor surface) of the finger F as radiant light L4. The radiant light L4, which contains a blood vessel pattern and is radiated again, is transmitted through the window 70. The light scattered at the surface of the finger is condensed by the individual lenses of the plane lens array 60 and shed on each element of the light receiving element array 50.

The light receiving element array 50 is a two-dimensional lattice array that uses individual photoelectric conversion elements to convert light to an electrical signal. The photoelectric conversion elements constituting the light receiving element array 50 measure approximately 0.02 mm by 0.02 mm in size when the elements constituting the transmission light quantity control element array 40 measure 0.3 mm by 0.3 mm in size. When the transmission light quantity control element array 40 is a lattice array that includes 100 horizontal elements and 140 vertical elements, the light receiving element array 50 is a lattice array that includes 100 horizontal photodiodes and 140 vertical photodiodes.

Examples of blood vessel patterns that are imaged by the personal identification device according to the present embodiment will now be described with reference to FIGS. 4A to 4C.

Figure 4A:
FIG. 4A shows a first example of a blood vessel pattern that is imaged by the personal identification device according to the first embodiment of the present invention.
Figure 4B:
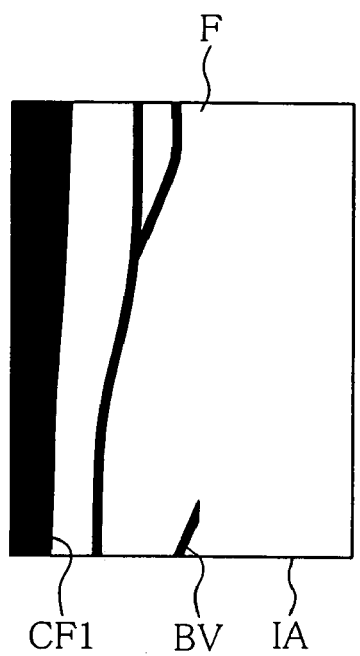
FIG. 4B shows a second example of a blood vessel pattern that is imaged by the personal identification device according to the first embodiment of the present invention.
Figure 4C:
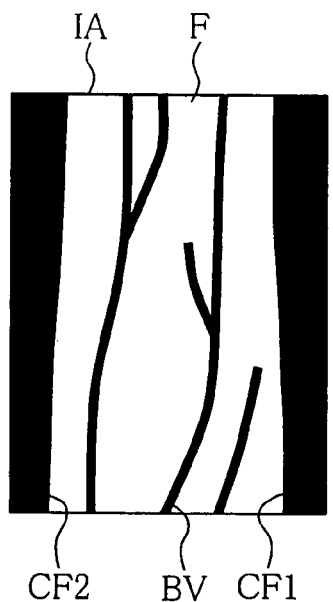
FIG. 4C shows an example of a combined blood vessel pattern that is obtained by the personal identification device according to the first embodiment of the present invention.

FIGS. 4A to 4C show examples of blood vessel patterns that are imaged by the personal identification device according to the first embodiment of the present invention.

FIG. 4A shows a blood vessel pattern that is obtained when the light is transmitted through a left-hand portion of the transmission light quantity control element array 40 as indicated in FIG. 3. The image picked up by the light receiving element array 50 contains a contour CF1 of one side of the finger F, which corresponds to a region where the light is blocked by the transmission light quantity control element array 40, and a part of a blood vessel pattern BV. As regards the left-hand portion of FIG. 4A, the light L1 emitted from the infrared light source 30 is reflected from the surface of the finger F and detected by the light receiving element array 50 as the reflected light L2. Since the quantity of detected light is large, the light receiving element array 50 becomes saturated. As a result, no blood vessel pattern is obtained as indicated by the left-hand portion of FIG. 4A.

FIG. 4B shows a blood vessel pattern that is obtained when the light is transmitted through a right-hand portion of the transmission light quantity control element array 40 in a situation where the transmission light quantity control element array 40 is configured as indicated in FIG. 3. In other words, when the light transmission region is changed to the opposite side, for instance, to a region between (x1, 1) and (xE, yE) in a situation where the transmission light quantity control element array 40 is configured as indicated in FIG. 3, a left-hand contour CF2 of the finger F and a part of the remaining portion of the blood vessel pattern BV are obtained.

FIG. 4C shows a combination of the right-hand image in FIG. 4A and the left-hand image in FIG. 4B. When the right- and left-hand images are combined in this manner, a blood vessel pattern BV of the entire finger F is obtained. The blood vessel pattern BV varies from one person to another. This blood vessel pattern BV or a pattern that is obtained as a result of image processing and feature extraction processing is pre-registered in the nonvolatile memory 24 and used as a registered pattern at the time of collation.

When the infrared light source and image pickup means are positioned on the same side of the finger, the light emitted from the infrared light source is reflected from the surface of the finger as described earlier. Since the image pickup means is saturated by such reflected light, the blood vessel pattern of the finger is not obtained. Under such circumstances, the infrared light source was previously positioned on both the right- and left-hand sides of the finger with the image pickup means positioned beneath the finger or the infrared light source was positioned above the finger with the image pickup means positioned below the finger. However, the use of these configurations increased the size of the personal identification device.

When, on the other hand, the infrared light source and image pickup means are positioned beneath the finger as described in conjunction with the present embodiment, the size of the personal identification device can be reduced. However, the light emitted from the infrared light source is reflected from the finger and the resulting reflected light is detected by the image pickup means. Thus, the image pickup means becomes saturated so that a good contrast, high-quality image cannot be obtained. Under these circumstances, the present embodiment further uses light quantity control elements to radiate a part of the finger with light and combine an image obtained when the finger is radiated from one side with an image obtained when the finger is radiated from the other side. In this manner, the present embodiment makes it possible to reduce the size of the personal identification device and produce good contrast images.

The presence or absence of the lens array for the personal identification device according to the present embodiment will now be described with reference to FIGS. 5A and 5B.

Figure 5A:
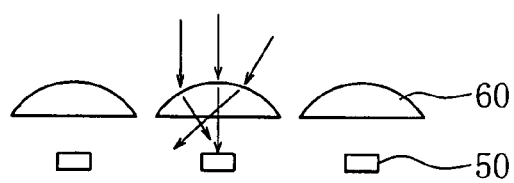
FIG. 5A illustrates a case where a lens array is included in the personal identification device according to the first embodiment of the present invention.
Figure 5B:
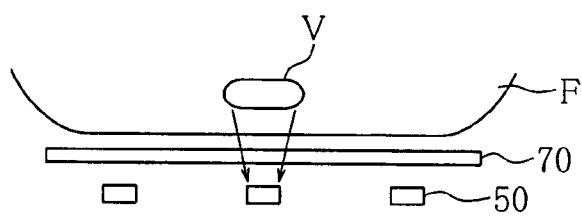
FIG. 5B illustrates a case where no lens array is included in the personal identification device according to the first embodiment of the present invention.

FIGS. 5A and 5B illustrate the presence or absence of the lens array for the personal identification device according to the first embodiment of the present invention.

In the embodiment shown in FIG. 1, the lens array 60 is positioned between the window 70 and light receiving element array 50 as described with reference to FIG. 1. The light that is reradiated from a blood vessel V is shed on the lens array 60 as light rays that are virtually parallel, as shown in FIG. 5A. Therefore, the reradiated light is photoelectrically converted with high efficiency by the light receiving surface of the light receiving element array 50, which is positioned at the focal position of the lens array 60. Meanwhile, the light reflected, for instance, from the surface of the finger F is obliquely shed on the lens array 60. Therefore, the reflected light is refracted by the lens array 60 and directed to a location away from the light receiving element array 50. Consequently, the reradiated light, which should be received, can be received efficiently.

When, on the other hand, the distance between the finger F and light receiving element array 50 is short as shown in FIG. 5B, the lens array is not always needed. In other words, the light that is reradiated from the blood vessel V of the finger F is photoelectrically converted with high efficiency by the light receiving element array 50.

A personal identification process that is performed in the personal identification device according to the present embodiment will now be described with reference to FIG. 6. An identification operation of the personal identification device 10 is performed by a program that is stored in the microcomputer 20, which is shown in FIG. 1.

Figure 6:
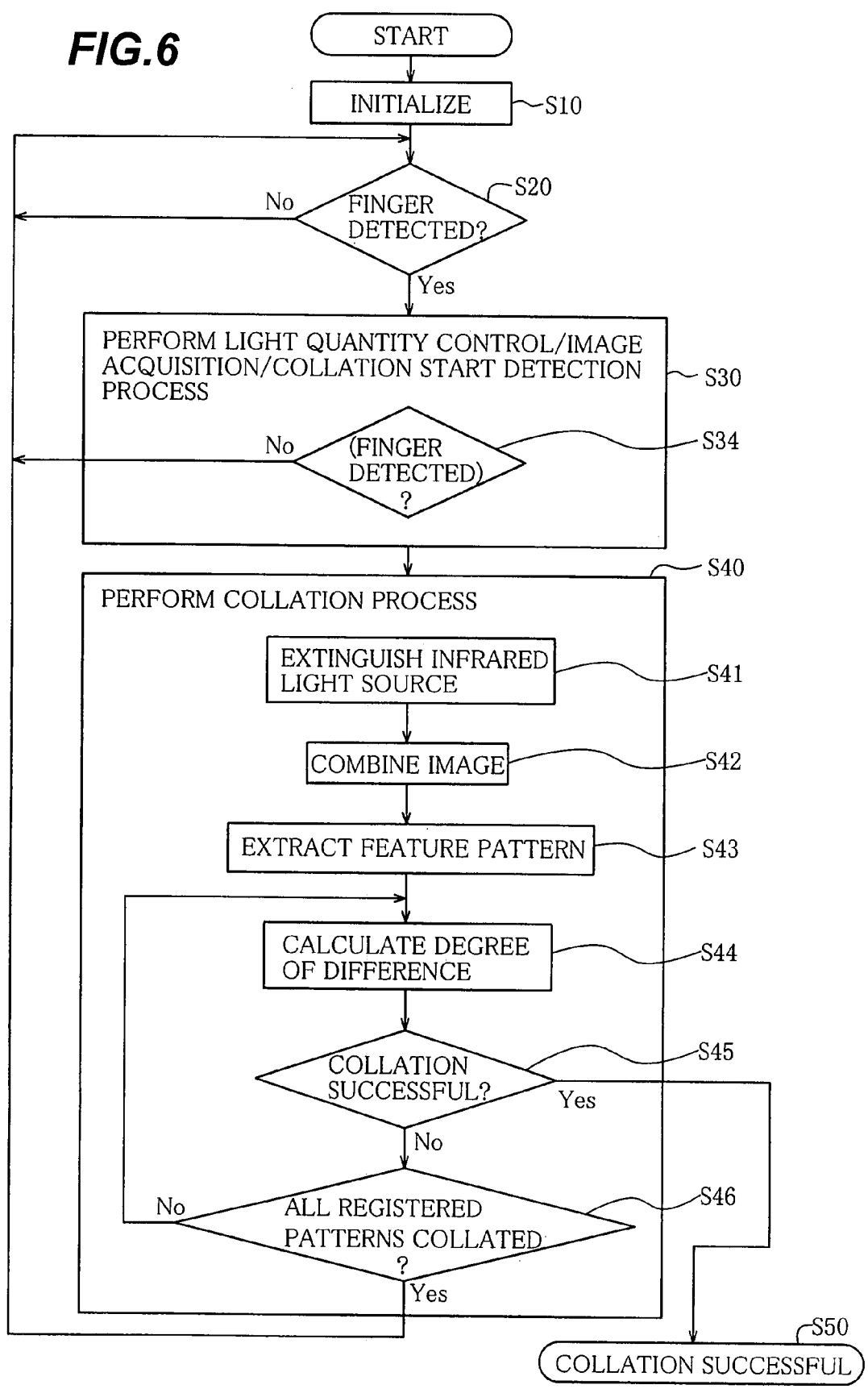
FIG. 6 is a flowchart illustrating a personal identification process that is performed by the personal identification device according to the first embodiment of the present invention.

FIG. 6 is a flowchart illustrating the personal identification process that is performed in the personal identification device according to the first embodiment of the present invention.

In step S10, the microcomputer 20 initializes the personal identification device 10.

Then, in step S20, the microcomputer 20 detects whether a finger F is positioned within a predetermined area. More specifically, when the switch 80, which is shown in FIG. 1, is turned on, the microcomputer 20 judges that the finger F is positioned within the predetermined area. If the finger F is detected, processing proceeds to step S30. If, on the other hand, the finger F is not detected, the microcomputer 20 repeatedly performs step S20 to detect the finger F.

When the finger F positioned within the predetermined area is detected, the microcomputer 20 follows step S30 to perform a light quantity control/image acquisition/authentication start detection process. Since the finger F might be removed during light quantity control, step S34 is followed as needed to perform a finger detection process. If the finger F is removed, processing returns to step S20.

In an image acquisition process, the microcomputer 20 operates the drive circuit 22 to illuminate the infrared light source 20. Further, the microcomputer 20 controls the transmission light quantity control element array 40 so that the light emitted from the infrared light source 20 is transmitted, for instance, through the left-hand elements in the transmission light quantity control element array 40 as shown in FIG. 3 to acquire the right-hand image of the finger F as shown in FIG. 4A. Next, the microcomputer 20 controls the transmission light quantity control element array 40 so that the light emitted from the infrared light source 20 is transmitted through the right-hand elements in the transmission light quantity control element array 40 to acquire the left-hand image of the finger F as shown in FIG. 4B. While the image acquisition process is being performed, the microcomputer 20 also performs a light quantity control process to control the quantity of light transmitted through each element in the transmission light quantity control element array 40 for the purpose of optimizing the quantity of light that falls on the finger F.

The light quantity control process that is performed by the personal identification device according to the present embodiment will be first described with reference to FIG. 7.

Figure 7:
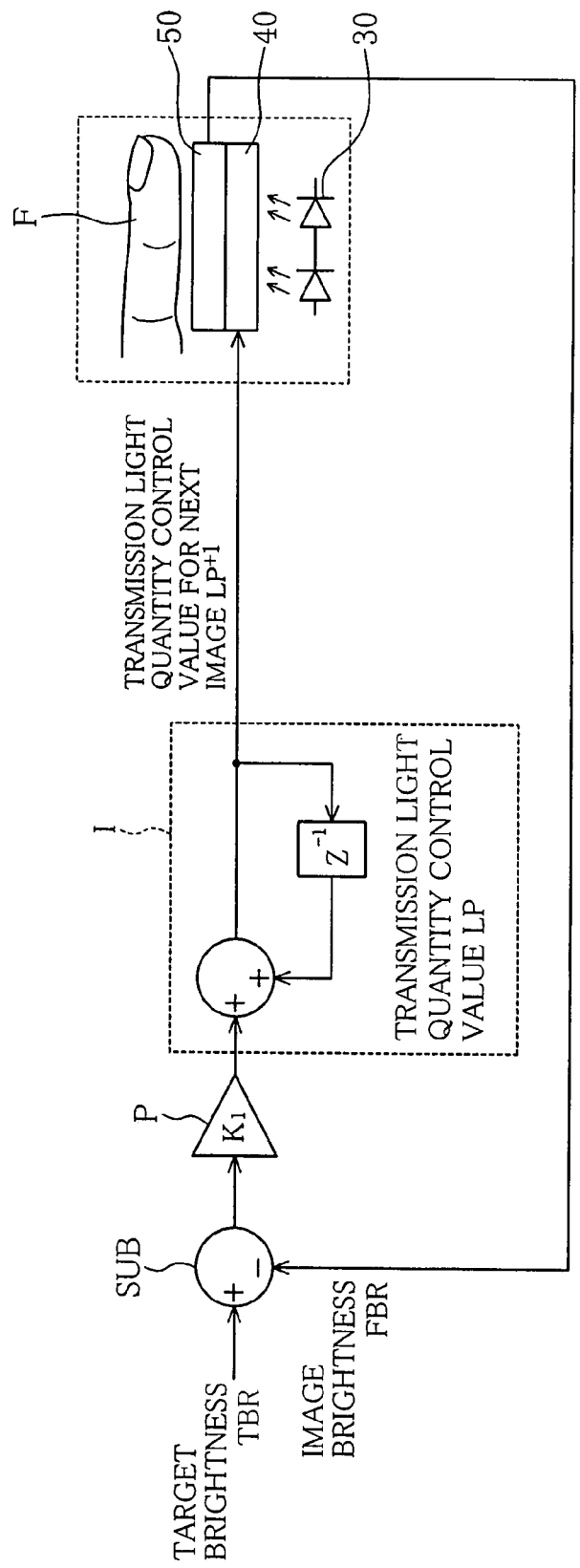
FIG. 7 is a control model diagram illustrating a light quantity control process that is performed by the personal identification device according to the first embodiment of the present invention.

FIG. 7 is a control model diagram illustrating the light quantity control process that is performed by the personal identification device according to the first embodiment of the present invention. The control model shown in this figure is executed by a program that is stored in the microcomputer 20.

A subtractor SUB determines the difference between the target brightness TBR of an image and the brightness FBR of an area in which a blood vessel pattern of the finger F captured by the light receiving element array 50 is obtained. A coefficient multiplier P determines a value that is obtained by multiplying the output of the subtractor SUB by a coefficient K1 (>0). An integrator I integrates the output of the coefficient multiplier P each time an image is acquired. In other words, the difference between the target brightness TBR and actually determined image brightness FBR is subjected to PI computation, and the output of the integrator I is used as a transmission light quantity control value $LP^{+1}$ in the transmission light quantity control element array 40 for acquisition of the next image. Briefly, negative feedback is performed by using the brightness FBR of an area in which a blood vessel pattern of the finger visible in an actually acquired image is obtained.

Therefore, if the brightness FBR of an area in which the finger's blood vessel pattern is obtained is lower than the target brightness TBR, the quantity of light transmitted through the transmission light quantity control element array 40 is increased. Thus, feedback is performed so as to increase the quantity of output light to be shed on the finger F. If, on the other hand, the brightness FBR of an area in which the finger's blood vessel pattern is obtained is higher than the target brightness TBR, feedback is performed so as to decrease the quantity of output light. This makes it possible to exercise detailed control over the elements of the transmission light quantity control element array 40 and acquire a uniformly bright, good contrast image within an area in which the finger's blood vessel pattern is obtained.

In step S30 in which the light quantity control/image acquisition/authentication start detection process is performed, an authentication start detection process is performed last. In this process, the microcomputer 20 judges whether a collation process should be started. This judgment is formulated depending on whether a stable image is obtained with the finger F set in position. When the difference between the target brightness TBR of the image and the brightness FBR of an area in which the finger's blood vessel pattern is obtained does not significantly vary, the microcomputer 20 judges that a stable image is acquired with a feedback loop stabilized.

Next, step S40 is followed to perform the collation process.

In step S41, the microcomputer 20 extinguishes the infrared light source 30.

In step S42, the microcomputer 20 produces an image by combining the left- and right-hand images obtained in the image acquisition process, which was performed in step S30.

In step S43, the microcomputer 20 performs computations on an acquired intensity distribution to calculate a feature pattern of a blood vessel pattern BV. This feature pattern is used as a collation pattern. The processing method for use in this step can be implemented by performing a filtering process that is formulated by combining an integral process and differential process as disclosed by JP-A-2001-184507.

In step S44, the microcomputer 20 collates the calculated collation pattern with one or more registered patterns that are previously stored in the nonvolatile memory 24. Here, the collation pattern calculated in step S43 is compared with a registered pattern, which is recalled from the nonvolatile memory 24, to calculate the degree of difference between the two patterns.

In step S45, the microcomputer 20 formulates a collation result judgment in accordance with the degree of difference, which was calculated in step S44. If the degree of difference is small, the microcomputer 20 judges that the finger belongs to a registered person, and processing proceeds to step S50. If, on the other hand, the degree of difference is great, the microcomputer 20 judges that the finger belongs to an unregistered person or concludes that collation has failed, and processing proceeds to step S46.

In step S46, the microcomputer 20 judges whether all the registered patterns have been collated. If all the registered patterns have been collated and there was no matching registered pattern, processing returns to step S20. If any registered pattern is left to be collated, processing returns to step S44 to repeat the collation process.

If, in step S45, the microcomputer 20 concludes that the finger belongs to a registered person, a command for permitting the doors to be unlocked or the engine to be started up can be issued in step S50.

As described above, the present embodiment can provide enhanced image quality because it positions the infrared light source and light receiving elements on the same side of the finger to reduce the thickness of the personal identification device, places the transmission light quantity control elements between the infrared light source and the finger to exercise control for the purpose of blocking or transmitting the light transmitted from the infrared light source, radiates a part of the finger with the transmitted light to acquire a left-hand image and a right-hand image, and combines these images.

The configuration of the personal identification device according to a second embodiment of the present invention will now be described with reference to FIG. 8.

Figure 8:
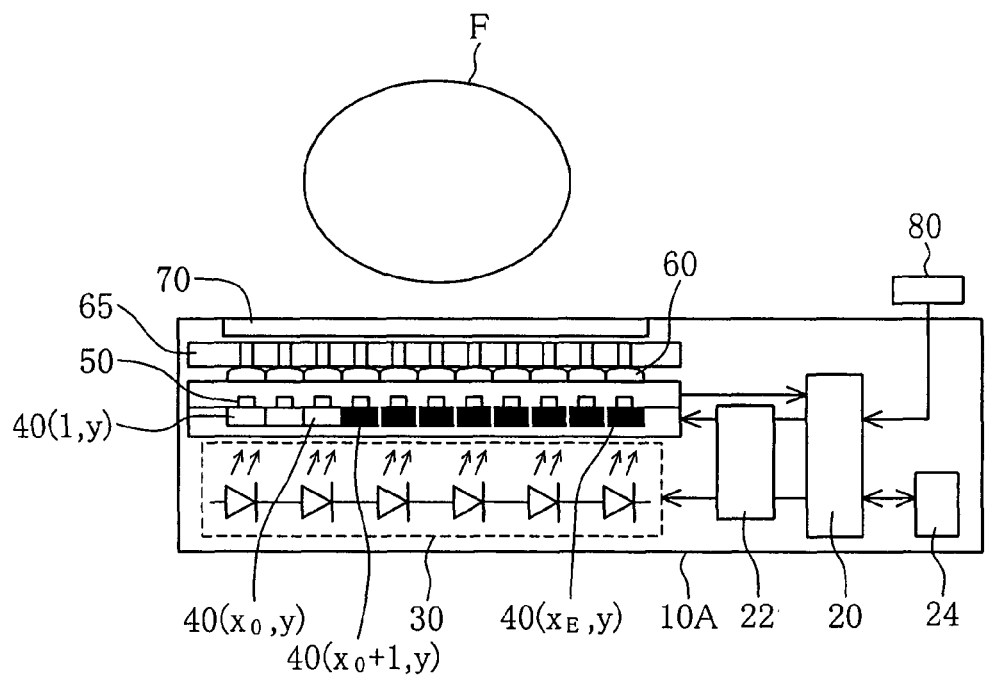
FIG. 8 is a cross-sectional view illustrating the configuration of the personal identification device according to a second embodiment of the present invention.

FIG. 8 is a cross-sectional view illustrating the configuration of the personal identification device according to the second embodiment of the present invention. Identical parts in FIGS. 1 and 8 are designated by the same reference numerals.

The personal identification device 10A according to the present embodiment differs from the personal identification device 10 shown in FIG. 1 in that the former includes an optical element 65. This optical element 65 is positioned toward the light receiving surface of the light receiving element array 50 so that only the light component vertically incident on the light receiving surface is allowed to pass through. A filter for causing light to propagate in a specific direction, such as 3M's light control film, can be used as the optical element 65.

The present embodiment can reduce the thickness of the personal identification device and eliminate light components that obliquely fall on the optical element 65. Therefore, the present embodiment makes it possible to obtain better contrast images.

The configuration of the personal identification device according to a third embodiment of the present invention will now be described with reference to FIG. 9.

Figure 9:
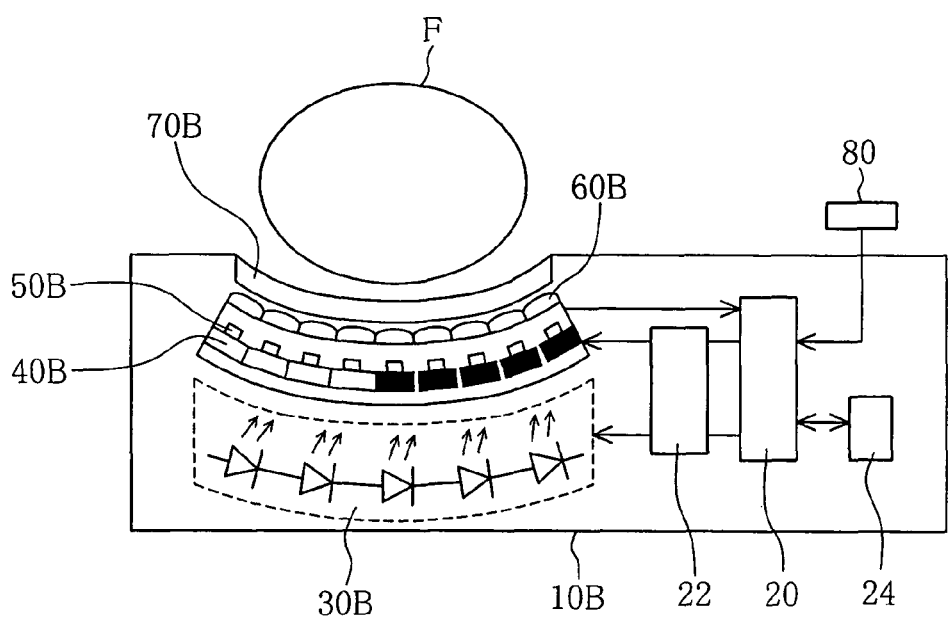
FIG. 9 is a cross-sectional view illustrating the configuration of the personal identification device according to a third embodiment of the present invention.

FIG. 9 is a cross-sectional view illustrating the configuration of the personal identification device according to the third embodiment of the present invention. Identical parts in FIGS. 1 and 9 are designated by the same reference numerals.

The personal identification device 10B according to the present embodiment differs from the personal identification device 10 shown in FIG. 1 in that the infrared light source 30B, transmission light quantity control element array 40B, light receiving element array 50B, lens array 60B, and window 70B have a curved surface shape and are arranged along the inner surface of the finger F.

In the above example, the infrared light source 30B, transmission light quantity control element array 40B, light receiving element array 50B, lens array 60B, and window 70B have a curved surface shape. However, the infrared light source 30B and transmission light quantity control element array 40B need not always have a curved surface shape.

The present embodiment makes it possible to reduce the thickness of the personal identification device, provide enhanced image quality, and readily indicate a position at which the finger F should be placed. Further, the obtained image has an axis in the direction of rotation around the finger axis. Therefore, even when the finger F rotates around the axis, the same pattern can be obtained although the position is changed.

The configuration of the personal identification device according to a fourth embodiment of the present invention will now be described with reference to FIG. 10.

Figure 10:
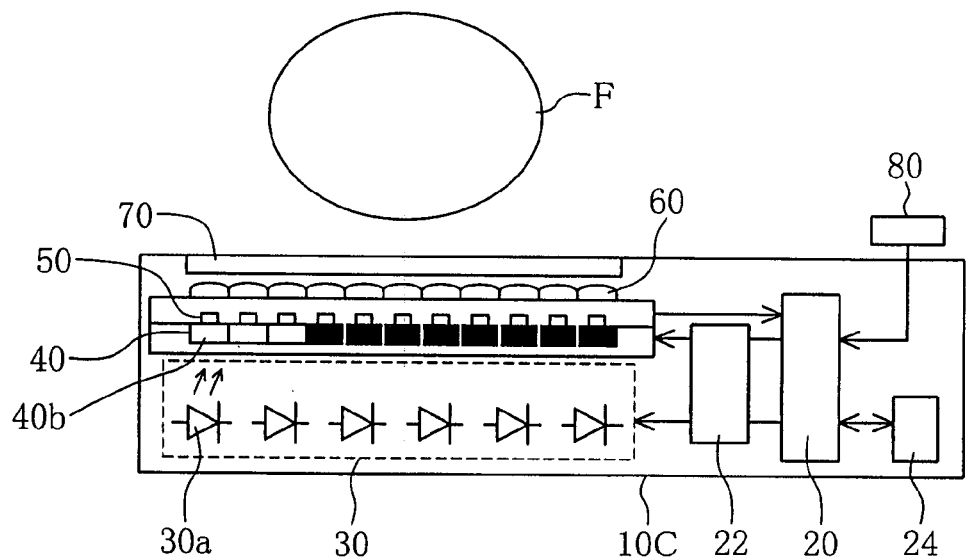
FIG. 10 is a cross-sectional view illustrating the configuration of the personal identification device according to a fourth embodiment of the present invention.

FIG. 10 is a cross-sectional view illustrating the configuration of the personal identification device according to the fourth embodiment of the present invention. Identical parts in FIGS. 1 and 10 are designated by the same reference numerals.

The personal identification device 10C according to the present embodiment differs from the personal identification device 10 shown in FIG. 1 in that the former illuminates some infrared light sources 30a of the infrared light sources 30. If the light is transmitted through the elements 40b of the transmission light quantity control element array 40 that are positioned on the left-hand side and shown in white in the figure, the infrared light sources 30a to be illuminated are within the range of the elements 40b that permit the light to pass through. The elements 40b that permit the light to pass through and the infrared light sources 30a that are to be illuminated can be changed as needed depending on a demanded image. Further, it is not necessary to illuminate all the infrared light sources 30 that are positioned within the range of the elements 40b through which the light is transmitted. When some of such infrared light sources are extinguished so that a reflected component, which is produced when the radiated light bounces off the surface of the finger F, enters the personal identification device 10C, it is possible to reduce the quantity of unnecessary re-reflected light that reaches the finger.

The present embodiment can reduce the thickness of the personal identification device, provide enhanced image quality, and decrease the number of infrared light sources 30 to be illuminated. Therefore, the present embodiment makes it possible to reduce the power consumption of the personal identification device 10C.

The configuration of the personal identification device according to a fifth embodiment of the present invention will now be described with reference to FIG. 11.

Figure 11:
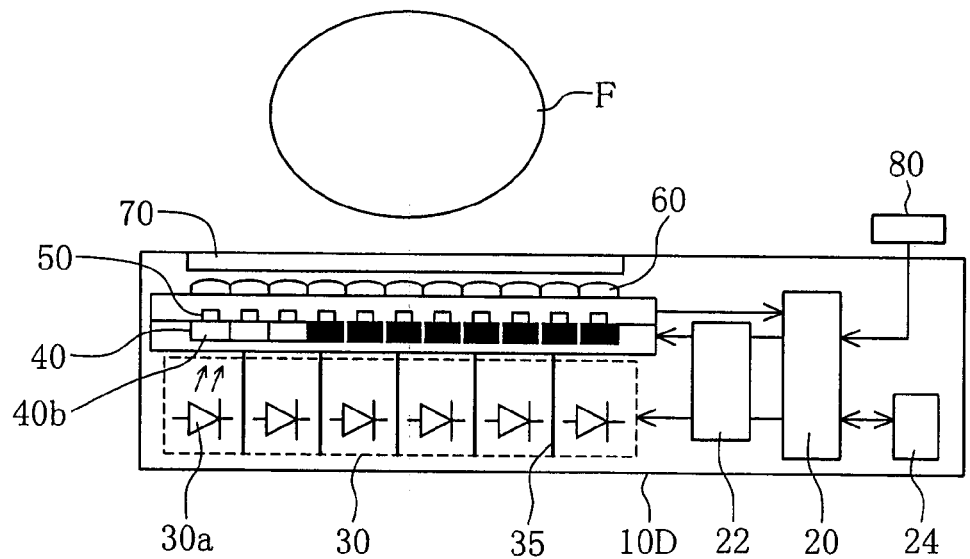
FIG. 11 is a cross-sectional view illustrating the configuration of the personal identification device according to a fifth embodiment of the present invention.

FIG. 11 is a cross-sectional view illustrating the configuration of the personal identification device according to the fifth embodiment of the present invention. Identical parts in FIGS. 1 and 11 are designated by the same reference numerals.

The personal identification device 10D according to the present embodiment differs from the personal identification device 10 shown in FIG. 1 in that a light shielding plate 35 is positioned between adjacent pairs of the infrared light sources 30. The light shielding plate 35 is formed, for instance, by applying light-absorbing paint to a plate material.

The present embodiment can reduce the thickness of the personal identification device and increase the quantity of light component that is vertically incident on the finger F, thereby making it possible to acquire good contrast images.

The configuration of the personal identification device according to a sixth embodiment of the present invention will now be described with reference to FIG. 12.

Figure 12:
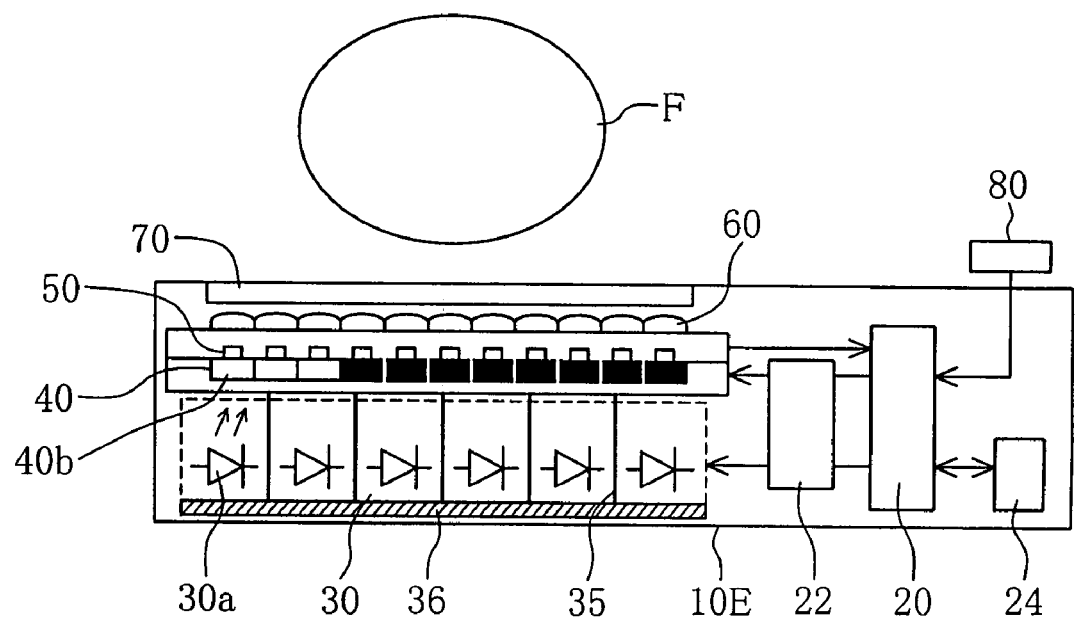
FIG. 12 is a cross-sectional view illustrating the configuration of the personal identification device according to a sixth embodiment of the present invention.

FIG. 12 is a cross-sectional view illustrating the configuration of the personal identification device according to the sixth embodiment of the present invention. Identical parts in FIGS. 1 and 12 are designated by the same reference numerals.

The personal identification device 10E according to the present embodiment differs from the personal identification device 10 shown in FIG. 1 in that the former includes a light absorber 36, which is positioned in a direction in which no light is radiated from the infrared light source 30.

The present embodiment can reduce the thickness of the personal identification device and absorb returning light that is directly reflected from the finger F, thereby making it possible to acquire good contrast images.

The configuration of the personal identification device according to a seventh embodiment of the present invention will now be described with reference to FIG. 13.

Figure 13:
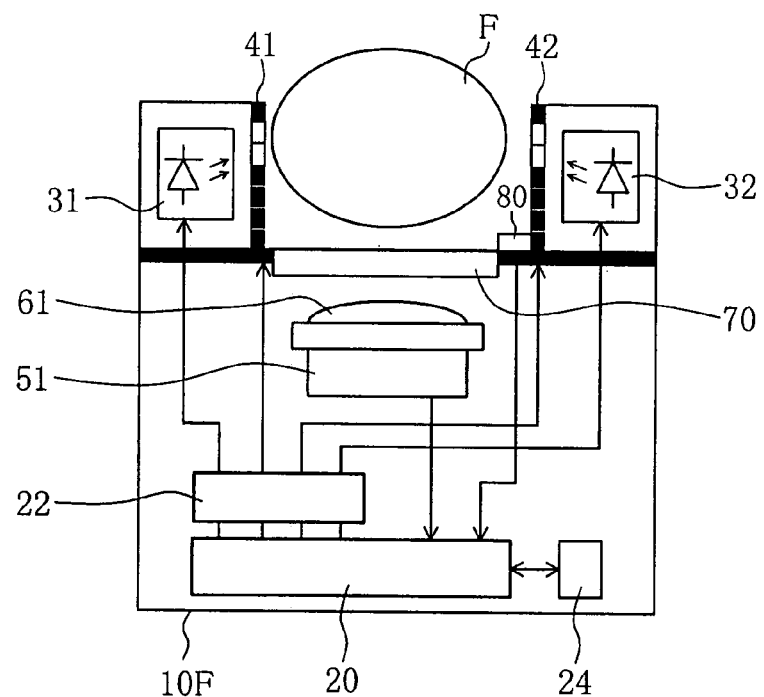
FIG. 13 is a cross-sectional view illustrating the configuration of the personal identification device according to a seventh embodiment of the present invention.

FIG. 13 is a cross-sectional view illustrating the configuration of the personal identification device according to the seventh embodiment of the present invention. Identical parts in FIGS. 1 and 13 are designated by the same reference numerals.

The personal identification device 10F according to the present embodiment differs from the personal identification device 10 shown in FIG. 1 in that the former uses two infrared light sources, which are a first infrared light source 31 and a second infrared light source 32, and a first transmission light quantity control element array 41 and a second transmission light quantity control element array 42, which correspond to the first infrared light source 31 and the second infrared light source 32, respectively. The first infrared light source 31 and the second infrared light source 32 face each other so that the finger F can be sandwiched between them.

The first transmission light quantity control element array 41 and the second transmission light quantity control element array 42 are used to provide light quantity control as described with reference to FIG. 7. Since the first infrared light source 31 and the second infrared light source 32 are positioned so that the finger F is sandwiched between them, the light reflected from the finger F does not directly fall on a light receiving element. Therefore, the overall blood vessel image of the finger F is obtained at one time instead of acquiring the left- and right-hand images and combining them as described in conjunction with the embodiment shown in FIG. 1.

An alternative would be to provide the two transmission light quantity control element arrays 41, 42 with significantly different transmission light quantities, let the transmission light quantity control element arrays 41, 42 have different transmission light quantities alternately to acquire images that look like FIGS. 4A and 4B, and combine the acquired images as shown in FIG. 4C.

Further, a lens 61 and an image sensor 51 are used for image acquisition. Here, a CCD image sensor or CMOS image sensor is used as the image sensor 51.

The present embodiment makes it possible to provide enhanced image quality and permits the use of a common CCD or CMOS image sensor.

The configuration of the personal identification device according to an eighth embodiment of the present invention will now be described with reference to FIG. 14.

Figure 14:
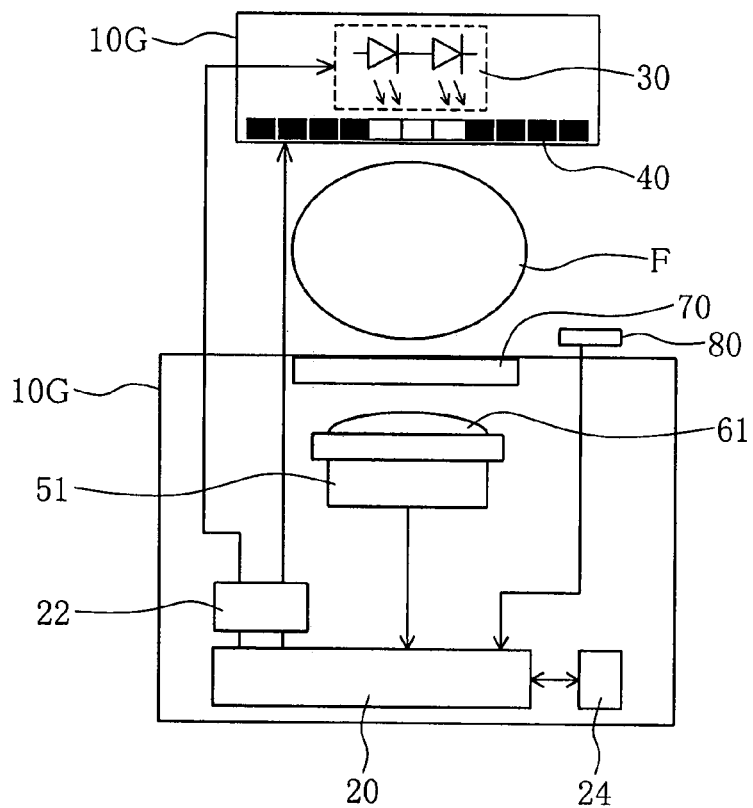
FIG. 14 is a cross-sectional view illustrating the configuration of the personal identification device according to an eighth embodiment of the present invention.

FIG. 14 is a cross-sectional view illustrating the configuration of the personal identification device according to the eighth embodiment of the present invention. Identical parts in FIGS. 13 and 14 are designated by the same reference numerals.

The personal identification device 10G according to the present embodiment differs from the personal identification device 10F shown in FIG. 13 in that the infrared light source 30 and transmission light quantity control element array 40 face the lens 61 and image sensor 51 with the finger F sandwiched between these two groups of parts.

Here, the first transmission light quantity control element array 40 is used to provide light quantity control in the same manner as indicated in FIG. 13. Since the infrared light source 30 and image sensor 51 are positioned so that the finger F is sandwiched between them, the light reflected from the finger F does not directly fall on a light receiving element. Therefore, the overall blood vessel image of the finger F is obtained at one time instead of acquiring the left- and right-hand images and combining them as described in conjunction with the embodiment shown in FIG. 1.

The present embodiment makes it possible to provide enhanced image quality and permits the use of a common CCD or CMOS image sensor.

The configuration of the personal identification device according to an eighth embodiment of the present invention will now be described with reference to FIG. 15.

Figure 15:
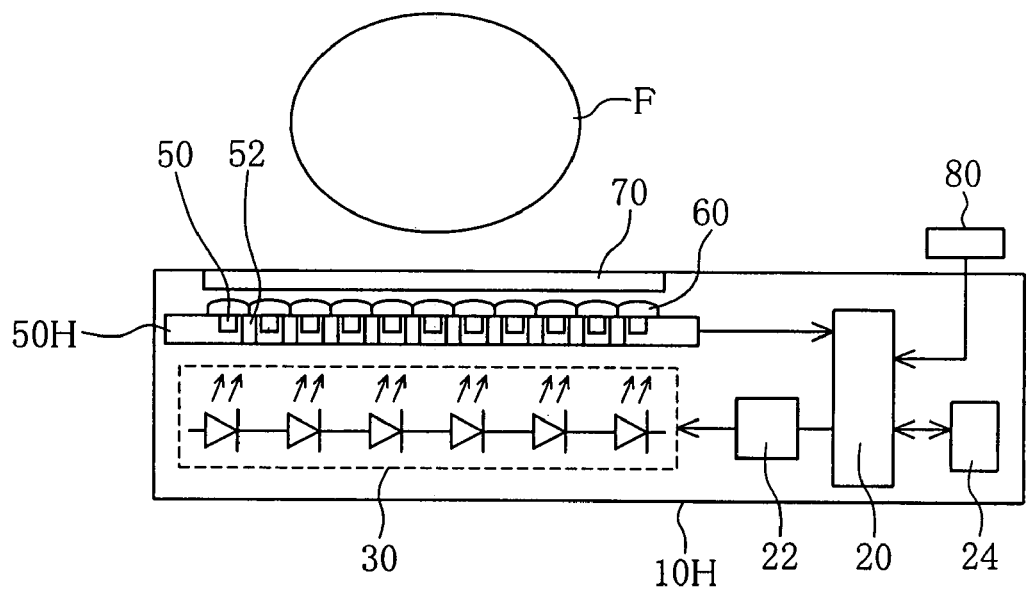
FIG. 15 is a cross-sectional view illustrating the configuration of the personal identification device according to a ninth embodiment of the present invention.

FIG. 15 is a cross-sectional view illustrating the configuration of the personal identification device according to the eighth embodiment of the present invention. Identical parts in FIGS. 1 and 15 are designated by the same reference numerals.

The personal identification device 10H according to the present embodiment differs from the personal identification device 10 shown in FIG. 1 in that the transmission light quantity control element array 40 shown in FIG. 1 is not used, and that a hole 52 is provided between a plurality of light receiving elements 50, which constitute the light receiving element array 50H on a silicon or other semiconductor substrate 52. The light emitted from the infrared light source 30 passes through the hole 53 and falls on the finger F. The light that contains a blood vessel pattern and is reradiated from the finger F is received by the light receiving element array 50H to acquire an image.

The present embodiment makes it possible to achieve a thin configuration.

The configuration of the personal identification device according to a ninth embodiment of the present invention will now be described with reference to FIG. 16.

Figure 16:
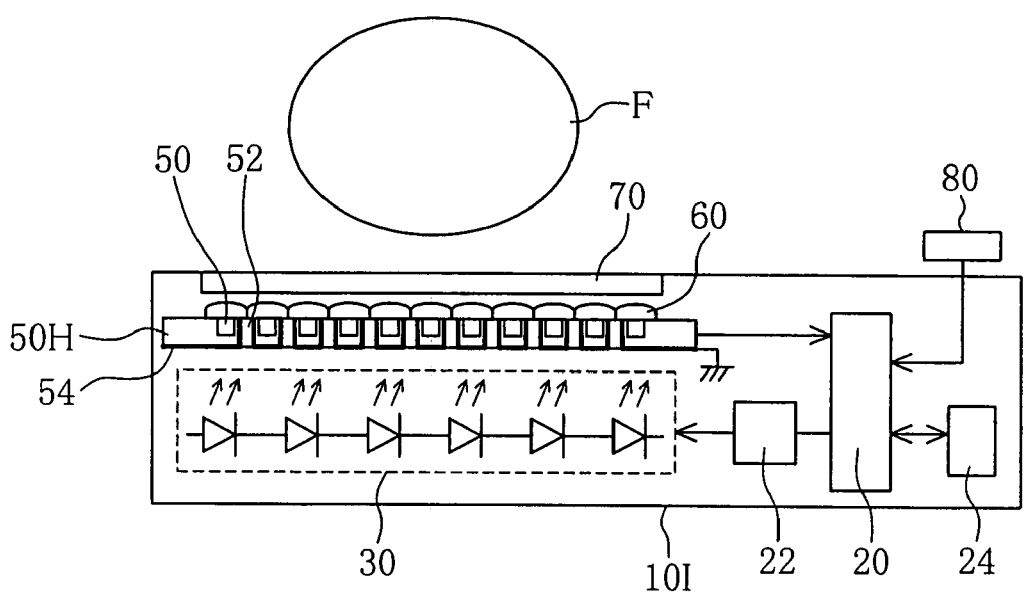
FIG. 16 is a cross-sectional view illustrating the configuration of the personal identification device according to a tenth embodiment of the present invention.

FIG. 16 is a cross-sectional view illustrating the configuration of the personal identification device according to the ninth embodiment of the present invention. Identical parts in FIGS. 15 and 16 are designated by the same reference numerals.

The personal identification device 10I according to the present embodiment differs from the personal identification device 10H shown in FIG. 15 in that the surface of the semiconductor substrate 52 on which no light receiving element 50 is mounted and the inner surface of the hole 53 are covered with a conductor 54. The conductor 54 is connected to ground potential. Since the surface of the semiconductor substrate 52 is covered with the conductor 54, the light emitted from the infrared light source 30 is not likely to produce a photoelectric effect. Further, even when electrons are excited, they can be absorbed by the conductor 54. This makes it possible to maintain the potential of the substrate at a fixed level and reduce noise in acquired images.

The present embodiment makes it possible to achieve a thin configuration and reduce noise in acquired images.

The configuration of the personal identification device according to a tenth embodiment of the present invention will now be described with reference to FIG. 17.

Figure 17:
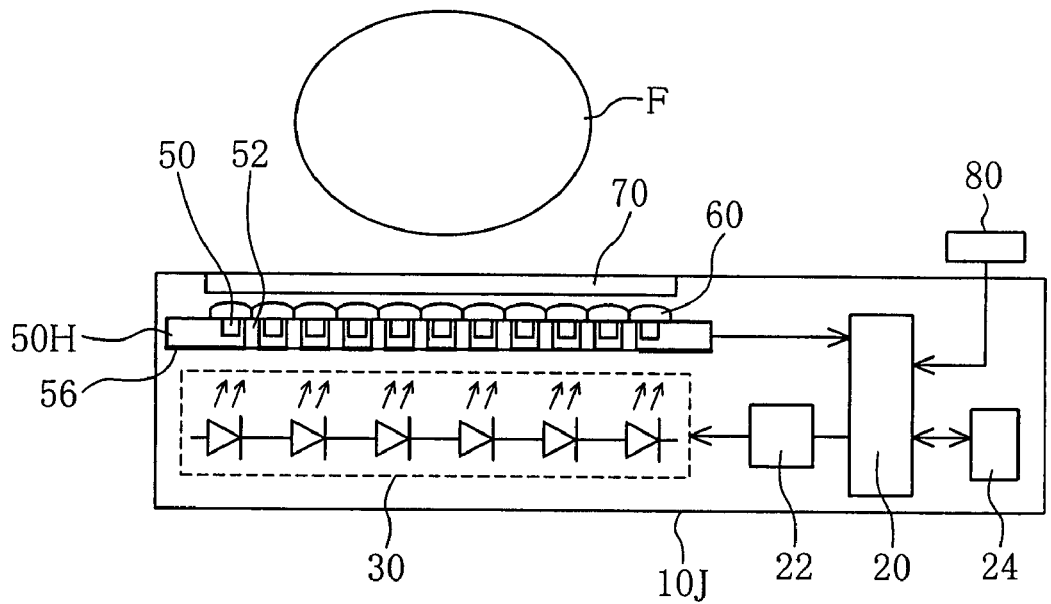
FIG. 17 is a cross-sectional view illustrating the configuration of the personal identification device according to an eleventh embodiment of the present invention.

FIG. 17 is a cross-sectional view illustrating the configuration of the personal identification device according to the tenth embodiment of the present invention. Identical parts in FIGS. 15 and 17 are designated by the same reference numerals.

The personal identification device 10J according to the present embodiment differs from the personal identification device 10H shown in FIG. 15 in that an opaque member 56 is positioned between the semiconductor substrate 52 and infrared light source 30. This opaque member 56 has a hole that is positioned the same as the hole 53 in the semiconductor substrate 52. Since the opaque member 56 is added as a cover, the light emitted from the infrared light source 30 is not likely to produce a photoelectric effect. Therefore, it is possible to maintain the potential of the substrate at a fixed level and minimize noise in acquired images.

The present embodiment makes it possible to achieve a thin configuration and reduce noise in acquired images.

The configuration of the personal identification device according to an eleventh embodiment of the present invention will now be described with reference to FIG. 18.

Figure 18:
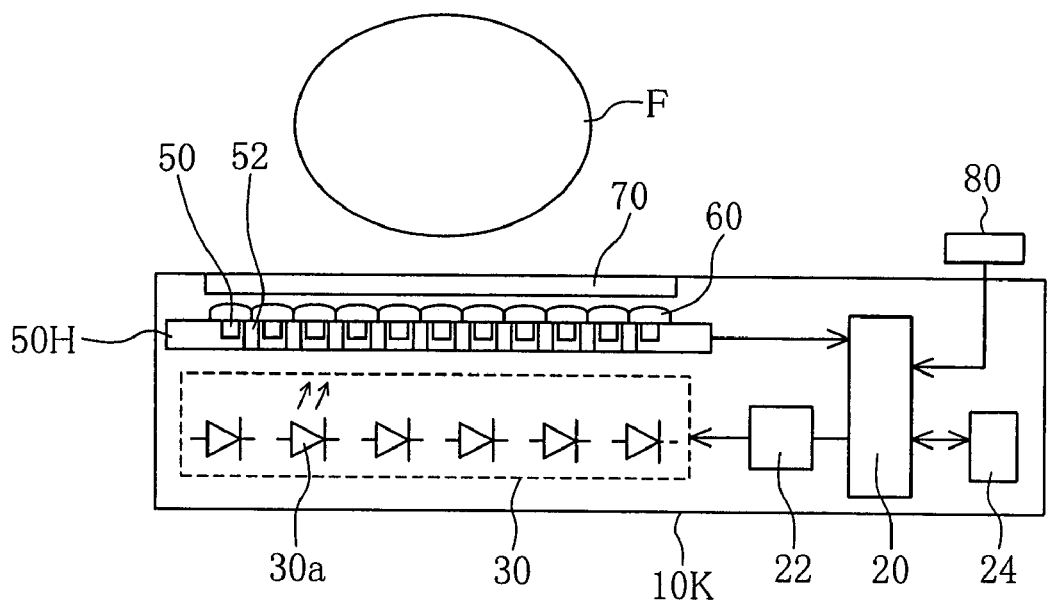
FIG. 18 is a cross-sectional view illustrating the configuration of the personal identification device according to a twelfth embodiment of the present invention.

FIG. 18 is a cross-sectional view illustrating the configuration of the personal identification device according to the eleventh embodiment of the present invention. Identical parts in FIGS. 15 and 18 are designated by the same reference numerals.

The personal identification device 10K according to the present embodiment differs from the personal identification device 10H shown in FIG. 15 in that the former illuminates some infrared light sources 30a of the infrared light sources 30.

The present embodiment makes it possible to achieve a thin configuration and reduce the power consumption of the personal identification device.

The configuration of the personal identification device according to a twelfth embodiment of the present invention will now be described with reference to FIG. 19.

Figure 19:
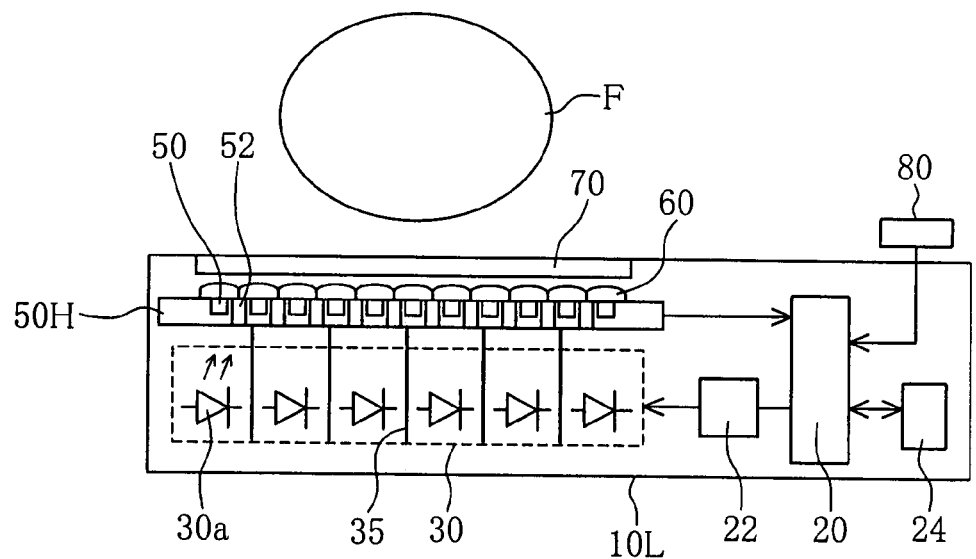
FIG. 19 is a cross-sectional view illustrating the configuration of the personal identification device according to a thirteenth embodiment of the present invention.

FIG. 19 is a cross-sectional view illustrating the configuration of the personal identification device according to the twelfth embodiment of the present invention. Identical parts in FIGS. 15 and 19 are designated by the same reference numerals.

The personal identification device 10L according to the present embodiment differs from the personal identification device 10H shown in FIG. 15 in that a light shielding plate 35 is positioned between adjacent pairs of the infrared light sources 30. The light shielding plate 35 is formed, for instance, by applying light-absorbing paint to a plate material.

The present embodiment can achieve a thin configuration and increase the quantity of light component that is vertically incident on the finger F, thereby making it possible to acquire good contrast images.

The configuration of the personal identification device according to a thirteenth embodiment of the present invention will now be described with reference to FIG. 20.

Figure 20:
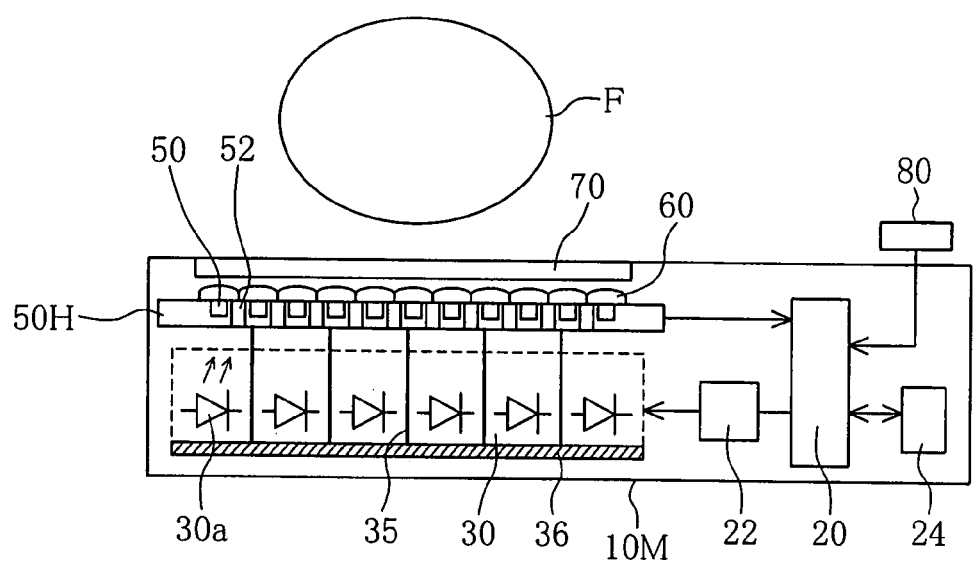
FIG. 20 is a cross-sectional view illustrating the configuration of the personal identification device according to a fourteenth embodiment of the present invention.

FIG. 20 is a cross-sectional view illustrating the configuration of the personal identification device according to the thirteenth embodiment of the present invention. Identical parts in FIGS. 19 and 20 are designated by the same reference numerals.

The personal identification device 10M according to the present embodiment differs from the personal identification device 10L shown in FIG. 19 in that the former includes a light absorber 36, which is positioned in a direction in which no light is radiated from the infrared light source 30.

The present embodiment can achieve a thin configuration and absorb returning light that is directly reflected from the finger F, thereby making it possible to acquire good contrast images.

The personal identification device described in conjunction with the foregoing embodiments can be used to issue a command for permitting a door to be unlocked or an engine to be started up or achieve personal authentication in an electronic toll collection (ETC) system. Further, the personal identification device can be embedded in transport machines such as automobiles, trains, and ships, input devices such as a keyboard or mouse for a personal computer, automated teller machines (ATMs) and cash dispensers (CDs) at a financial institution, cellular phones, doors to buildings, houses, and the like, and various other devices that require personal identification for entering or leaving a room or login authentication for using a computer.

The invention claimed is:

1. A personal identification device comprising:
an infrared light source;
a transmission light quantity control element array provided by a plurality of light transmission control elements for exercising control to transmit or block light radiated from said infrared light source to a living body; and
a light receiving element array provided by a plurality of light receiving elements for receiving light radiated from the living body;
wherein said infrared light source, said transmission light quantity control element array, and said light receiving element array are positioned on the same side of the living body; and
control identification means for identifying a person in accordance with a combined image that is obtained by combining a first image with a second image,
wherein said first image is obtained when said light receiving element array acquires light containing internal biometric feature information that is derived from the living body when said transmission light quantity control element array is controlled to radiate one region of the living body with light transmitted from said infrared light source; and
wherein said second image is obtained when said light receiving element array acquires light containing internal biometric feature information that is derived from the living body when said transmission light quantity control element array is controlled to radiate another region of the living body with light transmitted from said infrared light source.

2. The personal identification device according to claim 1, wherein said transmission light quantity control element array is made of a liquid-crystal material.

3. The personal identification device according to claim 1, wherein said transmission light quantity control element array and said light receiving element array are formed on a single transparent substrate.

4. The personal identification device according to claim 1, wherein an optical element is positioned toward a light receiving surface of said light receiving element array to permit the transmission of only a light component that is vertically incident on said light receiving surface.

5. The personal identification device according to claim 1, wherein at least said infrared light source, said transmission light quantity control element array, and said light receiving element array have a curved surface shape.

6. The personal identification device according to claim 1, wherein said infrared light source includes a plurality of infrared light sources; and wherein some of the plurality of infrared light sources illuminate in accordance with a region radiated by said transmission light quantity control element array.

7. The personal identification device according to claim 6, wherein a light shielding plate is positioned between adjacent pairs of the plurality of infrared light sources.

8. The personal identification device according to claim 1, further comprising:
a light absorber, which is positioned in a direction in which no light is radiated from said infrared light source.

* * * * *